United States Patent
Karas et al.

(10) Patent No.: US 7,022,885 B2
(45) Date of Patent: Apr. 4, 2006

(54) PURIFICATION ON METHYL TERTIARY BUTYL ETHER

(75) Inventors: Lawrence J. Karas, West Chester, PA (US); Lawrence M. Candela, Havertown, PA (US); Andrew P. Kahn, Eagleville, PA (US)

(73) Assignee: Arco Chemical Technology, L.P., Greenville, DE (US)

( * ) Notice: Subject to any disclaimer, the term of this patent is extended or adjusted under 35 U.S.C. 154(b) by 329 days.

(21) Appl. No.: 10/301,441

(22) Filed: Nov. 21, 2002

(65) Prior Publication Data

US 2004/0102656 A1 May 27, 2004

(51) Int. Cl.
*C07C 41/36* (2006.01)

(52) U.S. Cl. ........................... 568/699; 568/697

(58) Field of Classification Search ............... 568/699, 568/697

See application file for complete search history.

(56) References Cited

U.S. PATENT DOCUMENTS

| 4,605,787 | A |   | 8/1986  | Chu et al. ............ 568/697 |
|-----------|---|---|---------|---------------------------------|
| 4,814,517 | A |   | 3/1989  | Trubac ................. 568/697 |
| 5,401,887 | A |   | 3/1995  | Rastelli et al. ......... 568/697 |
| 5,457,243 | A | * | 10/1995 | Knifton et al. ......... 568/697 |
| 5,475,150 | A |   | 12/1995 | Rastelli et al. ......... 568/699 |
| 5,569,787 | A |   | 10/1996 | Rastelli et al. ......... 568/697 |
| 5,621,150 | A |   | 4/1997  | Rastelli et al. ......... 568/697 |
| 6,417,412 | B1|   | 7/2002  | Kahn et al. ............ 568/917 |

* cited by examiner

*Primary Examiner*—Rosalynd Keys
(74) *Attorney, Agent, or Firm*—William C. Long

(57) ABSTRACT

The present invention relates to purification of an MTBE process stream by contact in the liquid phase with a large pore zeolite such as 13X or Zeolite Y.

3 Claims, No Drawings

PURIFICATION ON METHYL TERTIARY BUTYL ETHER

BACKGROUND OF THE INVENTION

1. Field of the Invention

The present invention relates to the purification of methyl tertiary butyl ether (MTBE) and especially to the separation of minor amounts of close boiling oxygenated impurities therefrom by contacting the impure MTBE with a large pore zeolite such as 13x zeolite or zeolite Y.

2. Description of the Prior Art

Generally MTBE as produced by processes such as the reaction of isobutylene and methanol contains small but significant amounts of impurities including water, methanol, acetone, methyl ethyl ketone, tertiary butyl alcohol and the like. In certain applications the presence of such impurities causes problems with respect to the desired use. It is desirable to provide a process by which the impurities can be conveniently separated.

It is known that the close boiling oxygenated impurities can be separated to a significant degree from MTBE by an elaborate and extensive distillation procedure. However, such procedures are costly and time consuming, involving as they do substantial capitol investments and utilities expenses.

U.S. Pat. No. 5,401,887 shows treatment of ethyl tertiary butyl ether (ETBE) formed by reaction of isobutylene and ethanol and containing ethanol with zeolite 13X in order to remove ethanol. However, according to related U.S. Pat. No. 5,621,150 tertiary butyl alcohol (TBA) is not separated by the adsorptive treatment but remains with the ETBE.

U.S. Pat. No. 4,605,787 shows separation of methanol from MTBE and TBA by contact with a small pore zeolite. Example 19 demonstrates that TBA is not separated.

In many instances it is distinctly advantageous to separate from MTBE both the contained methanol and the contained TBA and the present invention provides such a procedure.

U.S. Pat. No. 6,417,412 shows the separation of various impurities from TBA by contact with a large pore zeolite such as 13X in the sodium form.

It is desirable to have a simplified procedure whereby MTBE process streams can be conveniently treated to separate close boiling impurities including methanol and TBA by a relatively simple and straight forward procedure.

SUMMARY OF THE INVENTION

In accordance with the present invention, an MTBE process stream, containing minor amounts of the impurities which are normally associated with the MTBE, is contacted in the liquid phase with a large pore zeolite such as 13x zeolite or zeolite Y, which may be in the sodium form. As a result of this contact, impurities such as methanol and TBA are retained on the zeolite and are thus removed or separated from the MTBE; product MTBE reduced in the content of contaminating impurities is readily recovered. It is generally advantageous to operate with a plurality of contact zones since the contact material must be regenerated from time to time as it loses its effectiveness for impurities removal over extended use. With a plurality of treatment zones, MTBE can be treated in one zone while a separate zone is being regenerated.

DETAILED DESCRIPTION

MTBE as produced commercially, for example by the reaction of methanol and isobutylene, contains small but significant amounts of impurities, e.g. 0.1 to about 2.0 wt %. Illustrative of such impurities are water, methanol, acetone, methyl ethyl ketone (MEK), TBA, and the like. The MTBE stream to be treated illustratively comprises by weight about 10 ppm to 2% of each of the above impurities, usually about 20 ppm to 1% of each. Other materials which can readily be separated as by distillation such as diisobutylene may also be present and do not interfere with the separation of the invention.

In accordance with the present invention, the impure MTBE in the liquid phase is contacted with solid large pore zeolite such as 13X zeolite or zeolite Y whereby impurities are retained on the contact zeolite solid and a liquid product MTBE reduced in impurities content is conveniently separated. The contact takes place at moderate temperatures, illustratively 0 to 150° C., although temperature is not critical. The contact solid retains the impurities adsorbed thereon and purified MTBE can be separated. Initially, there can be substantially complete removal of the impurities and the recovered MTBE is of exceptional purity. Over the course of time the contact solid gradually becomes less effective for the removal of these components, and at a predetermined time when the separation efficiency has fallen below a desired point, the solid contact material can be effectively regenerated, as by contact with a heated vapor stream such as nitrogen or air. It is advantageous to employ a plurality of parallel contact zones such that while one zone is being regenerated the feed is passed through a zone containing fresh or regenerated contact material so that optimum impurities removal can be achieved.

The zeolitic contact materials used in the present invention are those of large pore diameter (10 Angstroms) illustrated by 13x or zeolite Y; the large pore zeolites can be in the sodium or hydrogen form.

The large pore zeolites are useful for the removal of essentially all of the impurities as above described, which are normally associated with process streams, except diisobutylene which can readily be separated by distillation.

In order to illustrate practice of the invention the following examples are provided.

EXAMPLE 1

A 1.0 cm ID jacketed column was charged with 90 cc of Zeolite 13X which had been ground to 14/30 mesh and heated for 18 hours at 300° C. in nitrogen. A feed comprised of 97.5 wt % MTBE contaminated with 0.12% methanol, 0.37% acetone, 1.12% TBA, 0.15% methyl ethyl ketone and 0.27% diisobutylene was passed through the column at 25° C. at the rate of 90 cc/hr.

The first 75 cc of product recovered from the column showed complete removal of acetone and methyl ethyl ketone, 99.3% removal of TBA, and greater than 80% removal of methanol to give an MTBE product of about 99.3% purity.

EXAMPLE 2

A 1.5 cm ID column was charged with 48 cc of Zeolite 13X which had been ground to 30/50 mesh and dried in an oven overnight. A feed comprised of 99.7 wt % MTBE contaminated with 0.20 wt % TBA, 0.15 wt % acetone and 0.35 wt % MEK was passed through the column at 25° C. at the rate of 24 cc/h.

The first 288 cc of product recovered from the column showed complete removal of acetone and MEK and 98% removal of TBA to give an MTBE product of about 99.95% purity.

COMPARATIVE EXAMPLE 1

Example 2 was repeated using an activated carbon (48 cc, Calgon CAL 12×40). No enhancement of product purity was observed indicating that this material is unacceptable for MTBE purification.

COMPARATIVE EXAMPLE 2

Example 2 was repeated using 5A molecular sieves (48 cc, Grace Davision, 30/50 mesh). No removal of TBA and only a brief decrease of the acetone and MEK impurities was observed indicating that this small pore zeolite is unacceptable for MTBE purification.

The above results demonstrate that whereas the large pore zeolites effectively remove the various oxygenated impurities from MTBE, neither activated carbon nor smaller pore zeolite provides a comparable separation.

We claim:

1. The method of separating close boiling impurities from a MTBE process stream feed comprised mainly of MTBE and containing 0.1 to about 2.0 wt % of said impurities which comprises contacting the MTBE feed in the liquid phase with a solid contact material consisting essentially of a solid large pore zeolite and recovering a MTBE product stream reduced in content of said impurities from the contact.

2. The method of claim 1 wherein the zeolite is 13x.

3. The method of claim 1 wherein the zeolite is zeolite Y.

* * * * *